United States Patent [19]

Andrejasich

[11] Patent Number: 4,728,941

[45] Date of Patent: * Mar. 1, 1988

[54] FLUID DETECTION SYSTEM

[75] Inventor: Raymond J. Andrejasich, Carmel, Ind.

[73] Assignee: Emhart Industries, Inc., Indianapolis, Ind.

[*] Notice: The portion of the term of this patent subsequent to Apr. 29, 2003 has been disclaimed.

[21] Appl. No.: 801,918

[22] Filed: Nov. 26, 1985

Related U.S. Application Data

[62] Division of Ser. No. 579,431, Feb. 13, 1984, Pat. No. 4,586,033.

[51] Int. Cl.$^4$ .............................................. G08B 21/00
[52] U.S. Cl. .................................... 340/620; 340/624; 340/603; 73/40; 73/49.2
[58] Field of Search ............... 340/620, 624, 625, 602, 340/603, 604, 605, 618, 623, 580, 521, 522, 524, 517; 73/61.1 R, 40, 49.2, 40.5 R, 304 R, 308, 313, 73

[56] References Cited

U.S. PATENT DOCUMENTS

| | | | |
|---|---|---|---|
| 3,242,473 | 3/1966 | Shivers, Jr. et al. | 340/580 |
| 3,603,952 | 9/1971 | Smith | 340/603 |
| 3,651,330 | 3/1972 | Hayes | 340/603 |
| 3,873,927 | 3/1975 | Overall | 340/580 X |
| 4,126,857 | 11/1978 | Lancia et al. | 340/620 |
| 4,131,773 | 12/1978 | Maham et al. | 324/61 R X |
| 4,165,509 | 8/1979 | Betts et al. | 340/620 |
| 4,644,354 | 2/1987 | Kidd | 340/605 X |
| 4,646,069 | 2/1987 | Andrejasich et al. | 340/620 X |

Primary Examiner—Glen R. Swann, III
Assistant Examiner—Jeffery A. Hofsass
Attorney, Agent, or Firm—Carl A. Forest

[57] ABSTRACT

An apparatus for sensing the difference between a polar fluid and a non-polar fluid includes a control assembly, a probe assembly and a conduit electrically coupling the probe assembly to the control assembly at a remote location thereto. The probe assembly includes a float, at least one fluid sensor mounted beneath the float, a fluid sensor circuit for providing a signal indicative of the polar characteristics of the fluid, and a logic circuit having a first state when the signal indicates a polar fluid and a second state when the signal indicates a non-polar fluid. The control assembly includes cicuitry responsive to the state of the logic circuit for controlling alarms, visual indicators, and machine operations. The probe assembly may also include a detector for detecting the state of the fluid. If the fluid has a non-liquid state then the logic circuit has a third state which indicates the non-liquid state of the fluid. The probe assembly may also include a second fluid sensor mounted beneath the float in vertical spaced relationship to the one sensor.

4 Claims, 3 Drawing Figures

FLUID DETECTION SYSTEM

This application is a division of application Ser. No. 579,431, filed 2-13-84, now U.S. Pat. No. 4,586,033.

The present invention relates to fluid detectors that can detect the difference between polar and non-polar fluids, and more particularly to improvements in a fluid detector for detecting the presence of a hydrocarbon, such as gasoline, floating on water.

The contamination of ground water by various and sundry pollutants has been a problem in recent years. One such type of ground water contamination occurs when hydrocarbons, such as gasoline, leak undetected from underground storage tanks into the water table. Since underground fuel storage tanks are buried underneath the surface of the earth, leaks from these tanks often go undetected, resulting in several thousands of gallons of gasoline contaminating ground water. Underground fuel storage tanks are used extensively in the service station industry and therefore present the possibility of substantial contamination of the water table.

When an underground fuel storage tank leaks its contents undetected into the surrounding ground water, not only is the ground water contaminated but the party responsible for the fuel storage tank must often bear the cost of the clean-up. These costs can be substantial and, in the case of large spills, can easily run into millions of dollars. Further, many underground fuel storage tanks were installed during a "gas station boom" that occurred many years ago. These tanks are now beginning to corrode and leak, dramatically increasing environmental pollution hazards.

A problem with many hydrocarbon detectors is that they sense only the presence of a non-polar fluid. Since air is essentially a non-polar (non-conductive) fluid, as are hydrocarbons, these prior detectors trigger an alarm when either air or a hydrocarbon is present.

An object of the present invention is to provide a fluid detector that can detect the difference between polar and non-polar fluids and also detect the presence or absence of a liquid.

A further object of the present invention is to provide a fluid detector having a self-contained probe assembly located remote from a central control unit providing visual and audible alarms in response to a signal from the probe assembly.

Another object of the present invention is to provide a fluid detector having multiple probe assemblies coupled to a single central control unit for indicating the aggregate of the conditions being sensed by the probe units.

An apparatus constructed in accordance with the instant invention has a probe assembly which is located in a well drilled adjacent an underground fuel storage tank. A control assembly is located remotely from the well such as in the office of a service station. The control assembly includes visual indicators for indicating the status of the well and also includes an audible alarm for alerting the service station personnel when hydrocarbons are detected in the well. The probe assembly includes a float and a sensor for sensing the polar characteristic of fluid in the well. The probe assembly is located in the well and multiple probe assemblies can be coupled to one control assembly. Therefore, multiple wells can be drilled around the underground fuel storage tanks and be monitored by one control assembly. The probe assembly in each well also includes visual indicators for indicating the status of that individual well and also includes a push-button for actuating the indicators.

In one illustrative embodiment of the present invention, the probe assembly also includes a detector for detecting the state of the fluid. If the state of the fluid is not a liquid a signal is provided to give an indication of such state at the control assembly.

In another illustrative embodiment of the present invention two sensors are mounted to the float in vertical spaced relationship thereby requiring that both sensors sense a non polar fluid before activating an alarm or machine.

Additional features and advantages of the invention will become apparent to those skilled in the art upon consideration of the following detailed description of a preferred embodiment exemplifying the best mode of carrying out the invention as presently perceived. The detailed description particularly refers to the accompanying figures in which:

Figure 1:
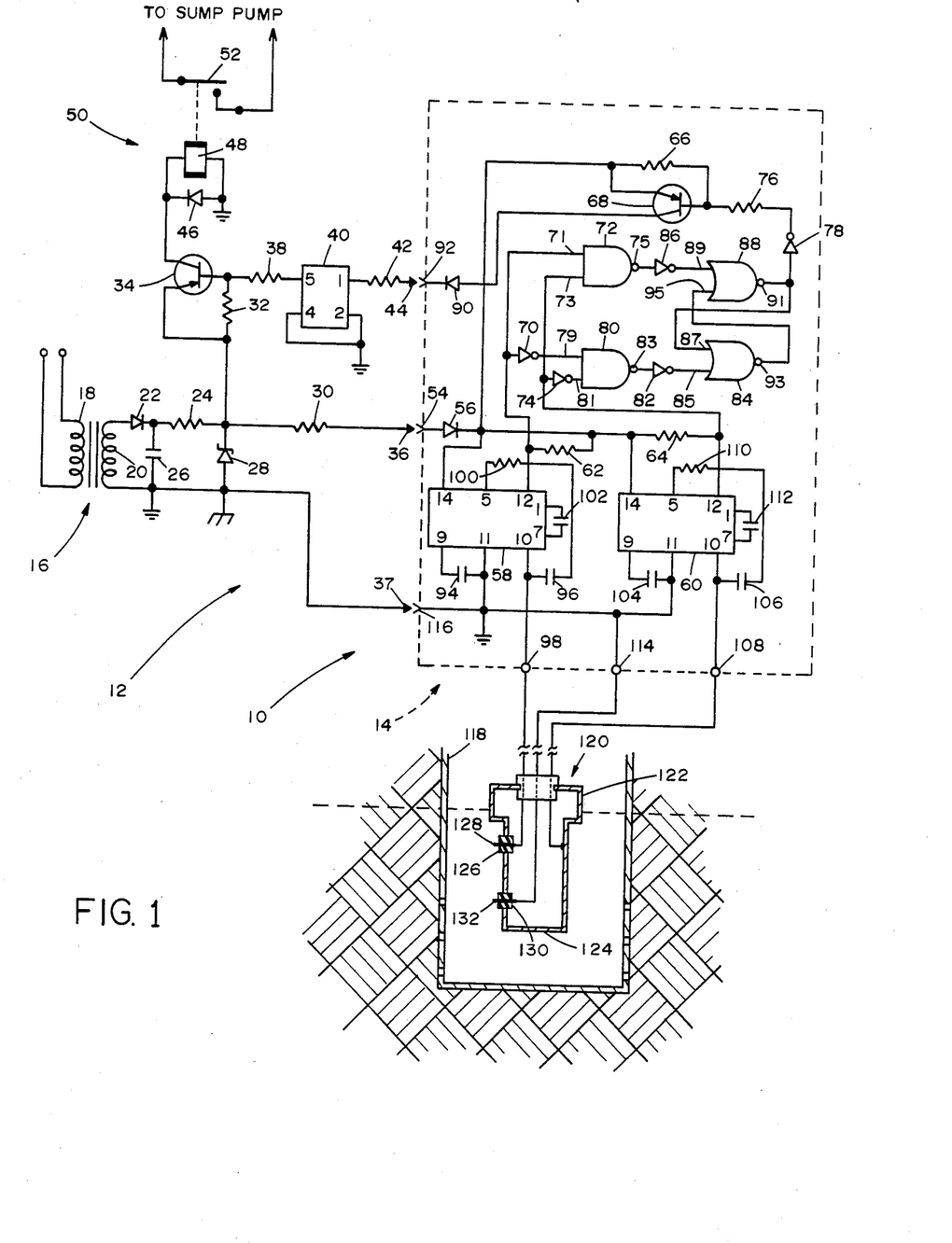
FIG. 1 is a schematic of one embodiment of the instant invention.

Referring to FIG. 1, an embodiment of the instant invention is shown. The fluid detector 10 has a control assembly 12 and a probe electronics assembly 14. The probe electronics assembly 14 is designed to be remotely located from the control assembly 12 and coupled thereto in a manner herein described.

Control assembly 12 includes a transformer 16 having a primary winding 18 and a secondary winding 20. Primary winding 18 is coupled to a source of A.C. electrical power in a conventional fashion. One side of secondary winding 20 is coupled to ground and the other side of secondary winding 20 is coupled to the anode of diode 22. The cathode of diode 22 is coupled to one side of resister 24 and the positive side of an electrolytic capacitor 26. The negative side of electrolytic capacitor 26 is coupled to ground. The other side of resistor 24 is coupled to the cathode of zener diode 28, one side of resistor 30, one side of resistor 32, and the emitter of transistor 34.

The anode of zener diode 28 is coupled to ground. The other side of resistor 30 is coupled to positive D.C. voltage output terminal 36. The other side of resistor 32 is coupled to the base of transistor 34 and to one side of resistor 38. The other side of resistor 38 is coupled to pin 5 (output) of opto-coupler 40. Pins 2 and 4 of opto-coupler 40 are each coupled to ground. Pin 1 (input) of opto-coupler 40 is coupled to one side of resistor 42. Opto-coupler 40 may be a TIL 116 of the type manufactured by Texas Instruments. The other side of resistor 42 is coupled to probe status input terminal 44. The collector of transistor 34 is coupled to the cathode of diode 46 and to one side of coil 48 of relay 50. The other side of coil 48 is coupled to ground as is the anode of diode 46. Contact 52 of relay 50 is connected to switch a sump pump (not shown) on or off according to the energization state of relay 50.

Probe electronics assembly 14 has D.C. power input terminal 54 coupled to the anode of diode 56. The cathode of diode 56 is coupled to pin 14 (Vcc) of fluid detector integrated circuit (IC) 58, pin 14 (Vcc) of fluid detector integrated circuit (IC) 60, one side of resistor 62, one side of resistor 64, one side of resistor 66 and to the emitter of transistor 68. The other side of resistor 62 is coupled to pin 12 (output) of fluid detector IC 58, the input of inverter 70, and to input 71 of NAND gate 72. The other side of resistor 64 is coupled to pin 12 (output) of fluid detector IC 60, the input of inverter 74, and input 73 of NAND gate 72. The other side of resistor 66 is coupled to the base of transistor 68 and to one side of resistor 76. The other side of resistor 76 is coupled to the output of inverter 78. In the illustrative embodiment, fluid detector IC's 58 and 60 may be a LM1830 fluid detector of the type manufactured by National Semiconductor Corporation.

The output of inverter 70 is coupled to input 79 of NAND gate 80 and the output of inverter 74 is coupled to the input 81 of NAND gate 80. The output 83 of NAND gate 80 is coupled to the input of inverter 82. The output of inverter 82 is coupled to input 85 of NOR gate 84. The output 75 of NAND gate 72 is coupled to the input of inverter 86 and the output of inverter 86 is coupled to input 89 of NOR gate 88. The output 91 of NOR gate 88 is coupled to the input of inverter 78 and to input 87 of NOR gate 84. The output 93 of NOR gate 84 is coupled to input 95 of NOR gate 88. As would be recognized by one skilled in the art, NOR gates 84 and 88 are interconnected in a S-R flip-flop configuration.

The collector of transistor 68 is coupled to the anode of diode 90 and the cathode of diode 90 is coupled to probe status output terminal 92. Pin 9 (filter capacitor terminal) of fluid detector IC 58 is coupled to the positive side of tantalum capacitor 94 and the negative side of tantalum capacitor 94 is coupled to pin 11 (ground) of fluid detector IC 58 and to ground. Pin 10 (input) of fluid detector IC 58 is coupled to one side of capacitor 96 and to probe input terminal 98. The other side of capacitor 96 is coupled to one side of resistor 100 and the other side of resistor 100 is coupled to pin 5 (oscillator output) of fluid detector IC 58. Pin 7 (oscillator capacitor terminal) of fluid detector IC 58 is coupled to one side of capacitor 102 and the other side of capacitor 102 is coupled to pin 1 (oscillator capacitor terminal) of fluid detector IC 58.

Pin 9 (filter capacitor terminal) of fluid detector IC 60 is coupled to the positive side of tantalum capacitor 104 and the negative side of tantalum capacitor 104 is coupled to pin 11 (ground) of fluid detector IC 60 and to ground. Pin 10 (input) of fluid detector IC 60 is coupled to one side of capacitor 106 and to probe input terminal 108. The other side of capacitor 106 is coupled to one side of resistor 110 and the other side of resistor 110 is coupled to pin 5 (oscillator output) of fluid detector IC 60. Pin 7 (oscillator capacitor terminal) of fluid detector IC 60 is coupled to one side of capacitor 112 and the other side of capacitor 112 is coupled to pin 1 (oscillator capacitor terminal) of fluid detector IC 60. A probe common terminal 114 is coupled to ground. Terminal 116 is also coupled to probe electronics assembly ground input terminal 37.

The fluid detector 10 just described operates to control a sump pump (not shown) in the following fashion. Transformer 18 steps the A.C. voltage to an appropriate level which is then rectified to a D.C. voltage by diode 22. Capacitor 26 filters the rectified D.C. voltage and zener diode 28 regulates the filtered D.C. voltage to provide a regulated D.C. voltage between positive D.C. voltage terminal 36 and ground terminal 37 through current limiting resistor 30. Terminals 36 and 37 are coupled to probe electronics assembly 14. Thus control assembly 12 provides the regulated D.C. voltage for probe electronics assembly 14. The regulated D.C. voltage is illustratively +15 VDC.

Probe electronics assembly 14 is remotely located from control assembly 12 generally in the well cap of a well as is more particularly described hereinafter. Probe electronics assembly 14 is coupled to control assembly 12 in a conventional fashion such as by wires. The D.C. power input terminal 54 of probe electronics assembly 14 is coupled to the D.C. output terminal 36 of control assembly 12. Probe electronics assembly ground input terminal 116 is coupled to ground terminal 37 of control assembly 12. Probe status output terminal 92 of probe electronics assembly 14 is coupled to probe status input terminal 44 of control assembly 12.

Two sets of probes are coupled to the probe electronics assembly 14. The probes are located in the well 118. Probe electronics assembly 14 is located in the well cap (not shown). Each probe set comprises a (first) probe coupled to pin 10 (input) of its respective fluid detector IC and a (second) probe coupled to pin 11 (ground) of its respective fluid detector IC. Illustratively, the second probes are also coupled to ground. Illustratively, the probe sets are held within well 118 by a probe-float assembly 120. Probe-float assembly 120 comprises float 122 having a downwardly extending conductive member 124 (second probe). Member 124 has a top insulative portion 126 in its side wall for holding a radially extending "high" probe 128 (first probe of one probe set) and a bottom insulative portion 130 in its side wall for holding a radially extending "low" probe 132 (first probe of the other probe set) in spaced vertical relationship beneath "high" probe 128. "High" probe 128 is coupled through probe input terminal 98 to pin 10 (input) of fluid detector IC 58 and the casing of conductive member 124 is coupled to prove common terminal 114. "High" probe 128 and member 124 thereby comprise the probe set for fluid-detector IC 58. "Low" probe 132 is coupled to probe input terminal 108 of fluid-detector IC 60. "Low" probe 132 and member 124 thereby comprise the probe set for fluid detector IC 60.

In the normal condition, when the high and low probes 128, 132 respectively are both surrounded by water, there are conductive paths through the water between the high probe 128 and the member 124 and between the low probe 132 and the member 124. The outputs on pins 12 (output) of fluid detector IC's 58, 60 will be high or a Logic "1". Oil or gasoline floating on the water will start to displace water around the float assembly 120 which holds the probes 128, 132. The high probe 128 will be surrounded by oil first, thereby breaking the conductive path between the high probe 128 and the member 124. At this point, the output on pin 12 (output) of fluid detector IC 58 will go low or to a Logic "0". As the oil film on the water builds up, the low probe 132 will be surrounded by oil, breaking the conductive path between the low probe 136 and the member 124. The output on pin 12 (output) of fluid detector IC 60 will then go low or to a Logic "0". At this point, the latch or flip-flop formed by NOR gates 84, 88 will be set. The output of the flip-flop (output 91 of NOR gate 88) after being inverted by inverter 78, will drive transistor 68 on or into a conductive state which will provide a positive D.C. voltage at the collector of transistor 68. This positive D.C. voltage is coupled through diode 90 to the probe status input terminal 44 of control assembly 12 via probe status output terminal 92 of probe electronics assembly 14. Probe status input terminal 44 is in turn coupled through opto-isolator 40 to the base of transistor 34 and will bias transistor 34 on or into a conductive state. When biased on, transistor 34 will energize coil 48 of relay 50 by providing a positive D.C. voltage to coil 48. Contacts 52 of relay 50 will close and activate a control circuit which illustratively will energize a sump pump (not shown) to begin pumping the oil from the well.

As the oil film recedes, the low probe 132 will again contact water and the output on pin 12 (output) of fluid detector IC 60 will go high or to Logic "1". However, this change in state will not reset the latch or flip-flop formed by NOR gates 84, 88. As the oil film continues to recede, the high probe 128 will again contact water. The output on pin 12 of fluid detector IC 58 will not go high or to Logic "1". This will cause the flip-flop formed by gates 84, 88 to be reset which will turn transistor 68 off. When transistor 68 is turned off, then transistor 34 is biased to an off state thereby de-energizing coil 48 of relay 50. Contacts 52 will then open and the sump pump (not shown) will thereby be turned off.

Illustratively, the circuit shown in FIG. 1 is designed so that the control assembly 12 is manufactured on a printed circuit board having an on-board voltage regulator (zener diode 28). The use of IC's with on-board voltage regulators allows the use of unregulated power supply lines. This means that instrumentation cable resistance (up to 40 ohms per line) will not affect performance. The illustrative probe electronics assembly 14 will work with voltages between 8 to 15 VDC.

In order to keep the voltage drop to a minimum across the instrumentation cables coupling the control assembly 12 to the probe electronics assembly 14, optocoupler IC 40 is used to keep the drive current for the relay 50 at about 10 mA instead of 100 mA. The use of IC's with on-board voltage regulators also allows current limiting wire-wound resistors to be used as protective components for intrinsic safety (I.S.). The current limiting resistor 42 for the L.E.D. in the opto-coupler isolator also becomes the current limiting protective component for I.S.

The 15 V Zener Diode 28 limits the voltage for the IC's to 15 VDC max. (CMOS IC range is 3–15 VDC). Wire-Wound Resistors 30 and 24 act as the current limiting protector device for I.S. In the illustrative embodiment shown in FIG. 1, the probe must be in a liquid environment to operate properly. Air appears to be non-polar (non-conductive) to the system. If the probes are in air, the system will give an alarm as if it were in a non-polar liquid such as oil. The liquid detector hereinafter described with respect to FIG. 2 may be used in applications where probes may be exposed to air. It will also be understood that the float assembly 120 could be placed between the inner and outer wall of a two-wall full storage tank.

Figure 2:
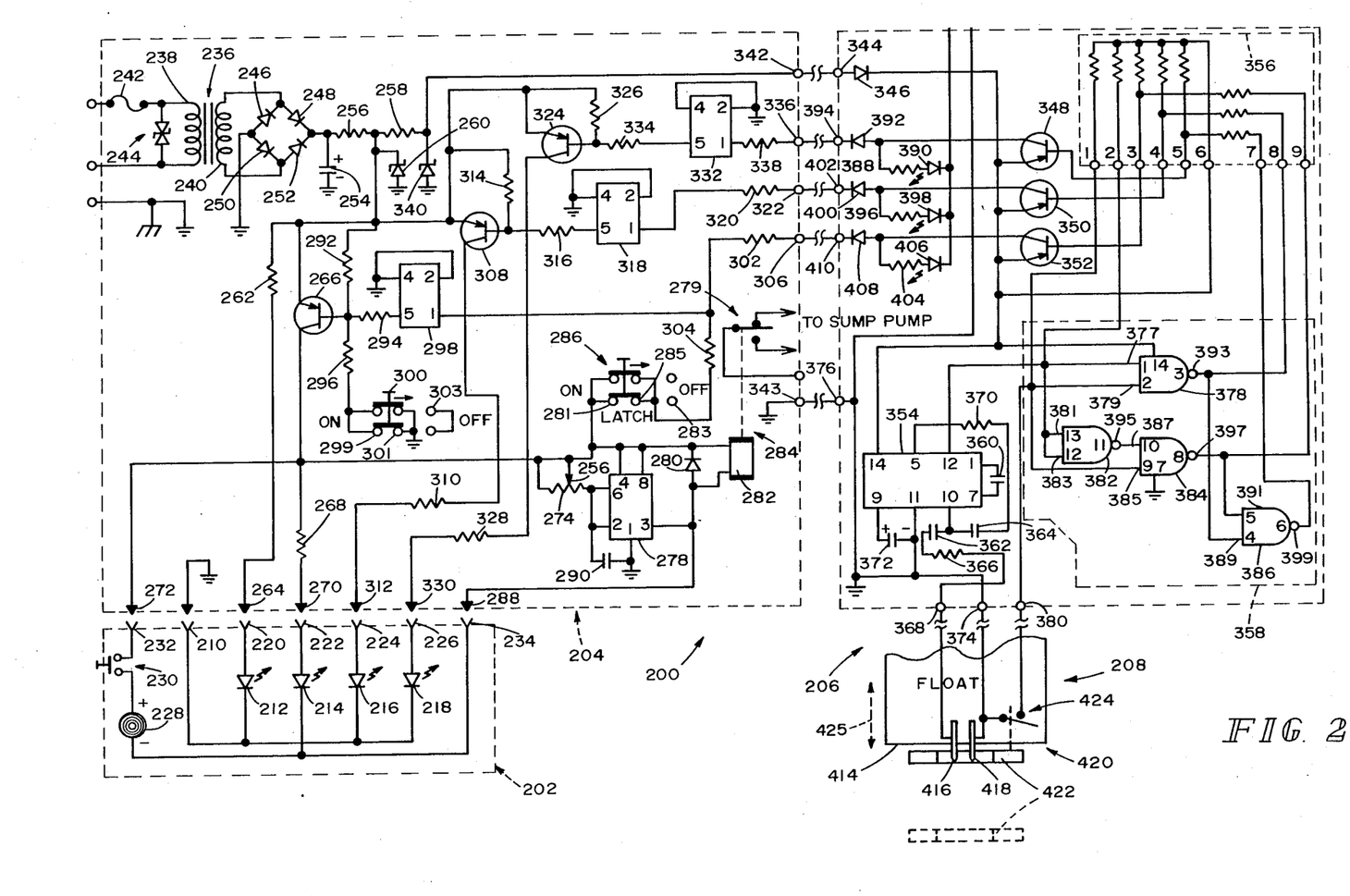
FIG. 2 is a schematic of another embodiment of the instant invention.

An embodiment of the fluid detector 200 shown in FIG. 2 has an enunciator panel 202, a control assembly 204, a probe electronics assembly 206, and probe unit 208. Enunciator panel 202 has ground terminal 210, and light emitting diodes (LED's) 212, 214, 216, and 218. The cathodes of LED's 212, 216, and 218 are each coupled to ground terminal 210. The cathode of LED 214 is coupled to alarm terminal 234. The anode of LED 212 is coupled to power status input terminal 220, the anode of LED 214 is coupled to oil status input terminal 222, the anode of LED 216 is coupled to water status input terminal 224, and the anode of LED 218 is coupled to air status input terminal 226. Illustratively, LED 212 is red and is illuminated when power is on to the fluid detector 200, LED 214 is red and is illuminated when the fluid detector detects the presence of a non-polar liquid, such as oil, LED 216 is yellow and is illuminated when the fluid detector 200 detects the presence of a polar liquid, such as water, and LED 218 is green and is illuminated when fluid detector 200 detects the absence of liquid.

Enunciator panel 202 further includes audible alarm 228 which is illustratively a SONALERT® alarm of the type manufactured by Emhart Industries, Inc. Alarm 228 has a plus terminal coupled to one side of audible alarm switch 230. The other side of audible alarm switch 230 is coupled to alarm input terminal 232. Audible alarm switch 230 is illustratively a push-on, push-off switch. Audible alarm 228 has a negative terminal coupled to alarm input terminal 234. It should be understood that audible alarm 228 could be any appropriate audible alarm device and audible alarm switch 230 could be any appropriate on-off switch.

Control assembly 204 includes a transformer 236 having a primary winding 238 and a secondary winding 240. Primary winding 238 has one side coupled to one side of an A.C. power source (not shown) through fuse 242. Illustratively, fuse 242 is a 1/16 amp. slow blow fuse. Primary winding 238 has its other side coupled to the other side of the A.C. power source. Primary winding 238 also has varistor 244 coupled in parallel which acts as a spike suppressor in a well known manner.

Secondary winding 240 has one side coupled to the cathode of diode 246 and to the anode of diode 248. The other side of secondary winding 240 is coupled to the cathode of diode 250 and to the anode of diode 252. The anodes of diodes 246 and 250 are coupled to ground and the cathodes of diodes 248 and 252 are coupled to the positive side of electrolytic capacitor 254 and to one side of resistor 256. As would be recognized by one skilled in the art, diodes 246, 248, 250, 252 are interconnected to form a full-wave bridge rectifier. The other side of electolytic capacitor 254 is coupled to ground. Capacitor 254 acts to filter the output of the full-wave bridge rectifier.

The other side of resistor 256 is coupled to the cathode of zener diode 260. The anode of zener diode 260 is coupled to ground. Zener diode 260 acts to regulate the D.C. voltage coupled to it through resistor 256 from the full-wave bridge rectifier to provide the positive D.C. voltage for control assembly 204, enunciator panel 202, and probe electronics assembly 206.

The cathode of zener diode 260 is coupled to one side of resistor 262 and the other side of resistor 262 is coupled to power output terminal 264. Power output terminal 264 is coupled to the power status input terminal 220 of enunciator panel 202 in a conventional fashion such as by a wire.

The cathode of zener diode 260 is also coupled to the emitter of transistor 266 which is illustratively a PNP transistor. The collector of PNP transistor 266 is coupled to one side of resistor 268. The other side of resistor 268 is coupled to oil status output terminal 270. Oil status output terminal 270 is coupled to the oil status input terminal of enunciator panel 202 in a conventional fashion such as by a wire.

The collector of transistor 266 is also coupled to alarm output terminal 272 which is coupled in a conventional fashion to the alarm input terminal 232 of enunciator panel 202. The collector of transistor 266 is also coupled to one side of potentiometer 274, the center tap 256 of potentiometer 274, pins 4 and 8 of IC 278, the cathode of diode 280, one side of coil 282 of relay 284, and to the "on" terminal 281 of slide switch 286.

The other side of coil 282 is coupled to the anode of diode 280, to pin 3 (output) of a timer integrated circuit (IC) 278, such as a LM 555 of the type manufactured by National Semiconductor Corporation. Coil 282 is also coupled to alarm output terminal 288. Alarm output terminal 288 is coupled to the alarm input terminal 234 of enunciator panel 202 in a conventional fashion.

Pin 1 (ground) of IC 278 is coupled to ground and to one side of capacitor 290. The other side of capacitor 290 is coupled to pins 2 (trigger) and 6 (threshold) of IC 278 and to the other side of potentiometer 274.

The cathode of zener diode 260 is also coupled to one side of resistor 292. The other side of resistor 292 is coupled to the base of transistor 266, to one side of resistor 294, and to one side of resistor 296. The other side of resistor 294 is coupled to pin 5 (output) of opto-coupler IC 298. The other side of resistor 296 is coupled to the "on" terminals 299 of slide-switch 300. The common terminals 301 of slide-switch 300 are coupled to ground and the "off" terminals 303 of slide-switch 300 are left open. When slide-switch 300 is moved to its "on" position, it couples "on" terminals 299 to ground. Pin 1 (output) of opto-coupler IC 298 is coupled to one side of resistor 302 and one side of resistor 304. The other side of resistor 302 is coupled to probe status input terminal 306.

The other side of resistor 304 is coupled to the common terminals 285 of slide-switch 286. The "off" terminals 283 of slide-switch 286 are left open. When slide-switch 286 is moved to its "off" position, the other side of resistor 304 is thereby allowed to float. When slide-switch 286 is moved to its "on" position, the other side of resistor 304 is coupled to alarm output terminal 272. Pins 2 and 4 of opto-coupler IC 298 are coupled to ground.

The cathode of zener diode 260 is further coupled to the emitter of transistor 308 which is illustratively a PNP type transistor. The collector of transistor 308 is coupled through resistor 310 to water status output terminal 312. Water status output terminal 312 is coupled to the water status input terminal 224 of enunciator panel 202.

The base of transistor 308 is coupled through resistor 314 to its emitter and through resistor 316 to pin 5 (output) of opto-coupler IC 318. Pins 2 and 4 of opto-coupler IC 318 are coupled to ground and pin 1 (input) of opto-coupler IC 318 is coupled through resistor 320 to probe status input terminal 322.

The cathode of zener diode 260 is also coupled to the emitter of transistor 324, which is illustratively a PNP type transistor, and to the base of PNP transistor 324 through resistor 326. The collector of PNP transistor 324 is coupled through resistor 328 to air output terminal 330. Air output terminal 330 is coupled in conventional fashion to the air status input terminal 226 of enunciator panel 202.

The base of PNP transistor 324 is also coupled to pin 5 (output) of opto-coupler IC 332 through resistor 334. Pins 2 and 4 of opto-coupler IC 332 are coupled to ground and pin 1 (input) of opto-coupler IC 332 is coupled to probe status input terminal 336 through resistor 338.

The cathode of zener diode 260 is also coupled to the cathode of zener diode 340 through resistor 258. The anode of zener diode 340 is coupled to ground. The cathode of zener diode 340 is also coupled to power output terminal 342. Zener diodes 260, 340 provide a regulated D.C. voltage to power output terminal 342.

Probe electronics assembly 206 has a power input terminal 344 which is coupled in conventional fashion to the power output terminal 342 of control assembly 204. Thus, it can be seen that control assembly 204 provides the power for probe electronics assembly 206. Power input terminal 344 is coupled to the anode of diode 346 and the cathode of diode 346 is coupled to the emitters of transistors 348, 350, and 352. Illustratively, transistors 348, 350, and 352 are PNP type transistors. The cathode of diode 346 is also coupled to pin 14 (Vcc) of fluid detector IC 354 and to pin 6 of resistor pack 356. The cathode of diode 346 is also coupled to pin 14 (Vcc) of integrated circuit (IC) 358. Illustratively, IC 358 is a MM 74C00 of the type manufactured by National Semiconductor Corporation and comprises four two-input NAND gates 378, 382, 384 and 386. Pin 7 (ground) of IC 358 is coupled to ground.

Fluid detector integrated circuit (IC) 354 illustratively is a LM 1830 of the type manufactured by National Semiconductor Corporation. Fluid detector IC 354 has its pin 1 (oscillator capacitor terminal) coupled to one side of capacitor 360 and its pin 7 (oscillator capacitor terminal) coupled to the other side of capacitor 360. Pin 10 (input) of fluid detector IC 354 is coupled to one side of capacitor 362 and to one side of capacitor 364. The other side of capacitor 362 is coupled through resistor 366 to positive probe input terminal 368. The other side of capacitor 364 is coupled through resistor 370 to pin 5 (oscillator output) of fluid detector IC 354. Pin 9 (filter capacitor terminal) of fluid detector IC 354 is coupled to the positive side of tantalum capacitor 372 and the negative side of tantalum capacitor 372 is coupled to ground. Pin 11 (ground) of fluid detector IC is also coupled to ground as is negative probe input terminal 374. Probe assembly 206 also has ground input terminal 376 coupled in a conventional fashion to control assembly ground terminal 343 providing a ground connection between the control assembly 204 and the probe electronics assembly 206.

Output pin 12 of fluid detector IC 354 is coupled to input 377 of NAND gate 378 (pin 1 of IC 358), inputs 381, 383 of NAND gate 382 (pins 12 & 13 of IC 358) and to pin 2 of resistor pack 356. Input 379 of NAND gate 378 (pin 2 of IC 358) is coupled to liquid detector input terminal 380. Output 395 of NAND gate 382 (pin 11 of IC 358) is coupled to input 387 of NAND gate 384 (pin 10 of IC 358). Input 385 of NAND gate 384 (pin 9 of IC 358) is coupled to the liquid detector input terminal 380 and to pin 1 of resistor pack 356. Output 397 of NAND gate 384 (pin 8 of IC 358) is coupled to input 391 of NAND gate 386 (pin 5 of IC 358) and to pin 9 of resistor pack 356. Output 393 of NAND gate 378 (pin 3 of IC 358) is coupled to input 389 of NAND gate 386 (pin 4 of IC 358) and to pin 8 of resistor pack 356. Output 399 of NAND gate 386 (pin 6 of IC 358) is coupled to pin 7 of resistor pack 356.

Pin 5 of resistor pack 356 is coupled to the base of PNP transistor 348, pin 4 of resistor pack 356 is coupled to the base of PNP transistor 350, and pin 3 of resistor pack 356 is coupled to the base of PNP transistor 352. The collector of PNP transistor 348 is coupled to the anode of diode 392 and through resistor 388 to the anode of LED 390. The cathode of diode 392 is coupled to probe status output terminal 394. Probe status output terminal 394 is coupled in a conventional fashion to probe status input terminal 336 of control assembly 204.

The collector of transistor 350 is coupled to the anode of diode 400 and through resistor 396 to the anode of LED 398. The cathode of diode 400 is coupled to probe status output terminal 402 which is coupled in conventional fashion to probe status input terminal 322 of control assembly 204.

The collector of PNP transistor 352 is coupled to the anode of diode 408 and through resistor 404 to the anode of LED 406. The cathode of diode 408 is coupled to probe status output terminal 410 which is coupled in conventional fashion to probe status input terminal 306 of control assembly 204.

The cathodes of LED's 390, 398, 406 are coupled to one side of normally open push-button switch 412. The other side of push-button switch 412 is coupled to the ground input terminal 376.

Resistor pack 356 comprises five pull-up resistors, each having one side coupled to the pack pin 6. Pin 6 is coupled to the positive D.C. voltage for probe electronics assembly 206 as heretofore described. The other side of the pull-up resistors are coupled to pins 1, 2, 3, 4, and 5 of resistor pack 356 respectively. Resistor pack 356 further includes three resistors coupled between pins 3 and 9, 4 and 8, and 5 and 7 respectively. Illustratively resistor pack 356 is a Cermet Resistor Network of the type manufactured by CTS CORP.

Probe unit 208 comprises float assembly 414 insulatively holding positive probe electrode 416 and negative probe electrode 418. Positive probe electrode 416 is coupled to positive probe terminal 368 of probe electronics assembly 206 and negative probe electrode 418 is coupled to negative probe input terminal 374 of probe electronics assembly 206. Float assembly 414 further includes liquid detector 420. Detector 420 includes a ceramic ring magnet 422 and magnetic reed switch 424. Magnetic reed switch 424 has one side coupled to negative probe electrode 418, and thereby to ground, and the other side coupled to liquid detector input terminal 380. A weighted ceramic ring magnet 422 is mounted in conventional fashion at the end of the float travel 425 beneath float assembly 414 in the bottom of the well.

Figure 3:
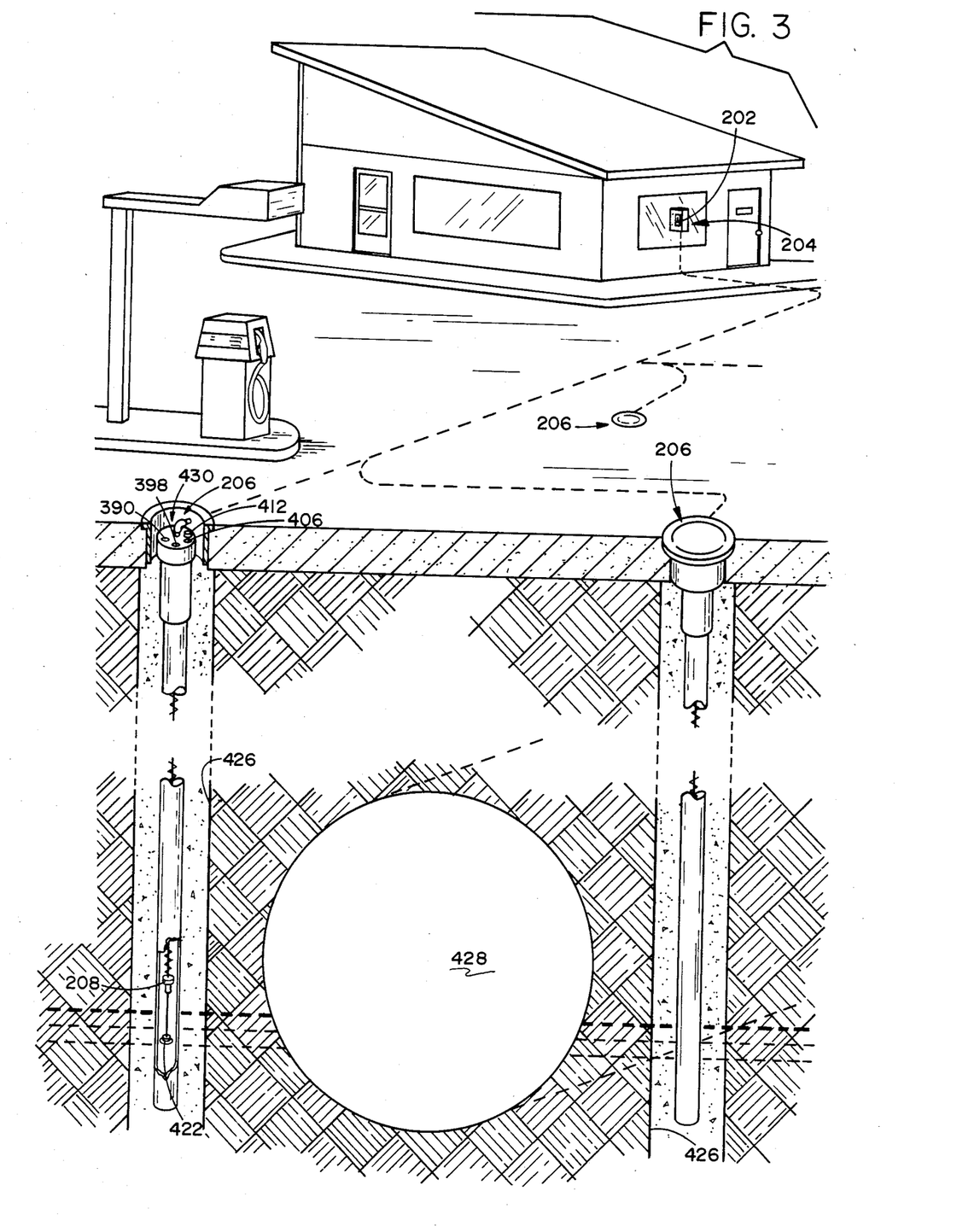
FIG. 3 is a diagrammatic view of the instant invention in its operative environment.

Referring to FIG. 3, a fluid detector 200 such as that shown in FIG. 2 is shown in its operative environment. The probe unit 208 is disposed within a well 426 drilled adjacent an in-ground gasoline fuel storage tank 428. Probe electronics assembly 206 is mounted in well cap 430 with LEDs 390, 398, 406 and push button switch 412 mounted to extend through the exterior of well cap 430. Control assembly 204 and enunciator panel 202 are remotely located from probe electronics assembly 206 in such a place as the office of a service station. Control assembly 204 is coupled to probe electronics assembly 206 in a conventional fashion such as by instrumentation wiring.

The fluid detector 200 can differentiate between the presence of air, water or hydrocarbons within the well 426. Further, multiple probe electronics assemblies 206 can be coupled to a single control assembly 204. Therefore, a single control assembly 204 and enuciator panel 202 can be utilized to indicate the status of multiple wells 426. The probe unit 208 can also be placed between the inner and outer walls of a two-wall in ground fuel storage tank 428 with the associated probe electronics assembly 206 mounted in the "well cap" of the tank.

The operation of fluid detector 200 is as follows. Float assembly 414 (FIG. 2) rides upon any liquid within well 426 and maintains probe electrodes 416, 418 in contact with the liquid. A weighted ceramic ring magnet 422 is at the end of float travel 425 (FIG. 2 and 3) in such a manner that, when the well 426 is dry, the float 414 will rest upon magnet 422 (FIG. 2) to activate magnetic reed switch 424. When there is liquid within well 426, the flotation of float 414 will carry it upwards away from magnet 422, causing magnetic reed switch 424 to deactivate. Liquid detector 420 therefore provides a high or logic "1" in liquids and a low or logic "0" in air. Liquid detector 420 could also comprise a differential pressure switch wherein the presence of a liquid causes a pressure change to activate the switch, a float actuated micro-switch, or a mercury switch in a float enclosure that is deflected as the level of the liquid changes to activate or de-activate the mercury switch.

Fluid detector IC 354 differentiates between polar fluids (water) and non-polar fluids (hydrocarbons). The output pin 12 of fluid detector IC 354 is high or logic "1" for a polar fluid (water) and low or logic "0" for a non-polar (hydrocarbon) fluid. Since the output pin 12 of fluid detector IC 354 is also low (0) when probe electrodes 416, 418 are in air, it is necessary to distinguish between the presence of air and the presence of liquid.

The output from liquid dector 420 and the output pin 12 of fluid detector IC 354 are coupled to a logic network comprising NAND gates 378, 382, 384, 386 in the manner heretofore described. Using A as the pin 12 output from fluid detector IC 354 and B as the output from liquid detector 420, the following truth table (Table II) was obtained:

TABLE II

| STATUS | A | B | (Output) (399) AIR | (Output) (397) OIL | (Output) (393) WATER |
|---|---|---|---|---|---|
| Air | 0 | 0 | 0 | 1 | 1 |
| Water | 1 | 1 | 1 | 1 | 0 |
| Oil | 0 | 1 | 1 | 0 | 1 |
| Invalid | 1 | 0 | 1 | 1 | 1 |

The outputs from NAND gates 378, 382, 384, 386 are combined in the fashion heretofore described and are coupled to the bases of transistors 348, 350, 352 to provide status signals at probe status output terminals 394, 402, 410 indicative of the condition sensed by probes 416, 418 and liquid detector 420 and to illuminate the appropriate LEDs 390, 398, 406.

In the embodiment shown in FIG. 2, LED 390 and the signal at probe status output terminal 394 are indicative of whether probes 416, 418 are sensing air or liquid within well 426. LED 398 and the signal at probe status output terminal 402 will, when in an "on" state, indicate that probes 416, 418 have sensed the presence of a polar liquid (water). LED 406 and the corresponding signal at probe status output terminal 410 will indicate, when in an "on" condition, that probes 416, 14 are sensing the presence of a non-polar liquid (hydrocarbons).

By mounting fluid detector IC 354 with the associated electronics in the well cap to provide the appropriate output signals on the output terminals 394, 402, 410 of probe electronics assembly 206, problems heretofore caused by the capacity of long cable lengths between probe electrodes 416, 418 and the fluid detector IC 354 are eliminated. Therefore, the maximum cable length that can be used to couple the probe electronics assembly 206 to the control assembly 204 is now only a function of maximum permissible power losses due to cable resistance. In the embodiment shown in FIG. 2, the maximum cable length is in the range of 1,000 to 4,000 feet.

Continuing to refer to FIG. 2, diodes 346, 392, 400, and 408 provide isolation of the electronic components in probe electronics assembly 206 from control assembly 204 to prevent possible destruction of the probe by incorrect wiring to control assembly 204. Further, diodes 392, 400, 408 could be the LED's used to provide the well head probe status indicators which are provided by LEDs 390, 398, 406 in FIG. 2. However, to keep the voltage to a minimum across the instrumentation cables, the push-to-test feature provided by push button 412 is used to give momentary status displays, one probe at a time.

Since the fluid detector 200 of the instant invention is for use in hazardous locations such as in gasoline storage tanks, certain safety features are mandated. Transformer 236 of control assembly 204 is a low cost split-bobbin power transformer meeting the requirements for Class I, Division 1, Group D hazardous locations. Protective current-limiting resistors required by FM (Factory Mutual which promulgates standards for "intrinsically safe" products) and UL (Underwriters Laboratory) were used in conjunction with 15 volt zener diodes 260, 340 to supply an initial 15 volts to the common and power output terminals 342, 343. As additional probes are coupled to control assembly 204, the voltage at power output terminal 342 can drop down to 8.5 volts without any deterioration in system performance.

Control assembly 204 causes the appropriate LED of enunciator panel 202 to be illuminated in response to the probe status signals received from probe electronics assembly 206. This provides a visual display at a central location indicative of the status at the wells determined by their respective probes. Enunciator panel 202 is illustratively the front panel of an enclosure housing control assembly 204. Push button 412 of probe electronics assembly 206 at the well cap provides an instant display of the status of the respective well at the well head. By utilizing the push-to-test technique, the LEDs used to indicate the status of the well at the well head need not be constantly energized thereby saving power.

Resistors 256, 258 and 302, 320, 338 are protective components to provide current limiting for intrinsic safety. They also protect the control assembly electronics in case the wire terminations from the probe electronics assembly 206 are wired to the control assembly 204 improperly or if the instrumentation wiring were to short out. In either case, the resistors act as current limiters and dissipate any excessive power created by an external fault.

ICs 298, 318, 332 are opto-couplers that provide two functions. They translate any voltage appearing on their respective probe status input terminals 336, 322, 306 into a "switch closure" (solid state) to bias their respective transistor switch 324, 308, 266 on. Transistors 324, 308, 266 will then illuminate their respective LEDs 218, 216, 214 of enunciator panel 202. As the opto-couplers 332, 318, 266 use LED transmitters driving photo transistors, the LEDs will trigger the photo transistors over a wide range of LED drive currents. As the voltages on probe status input terminals 336, 322, 306 are converted to LED drive currents by resistors 338, 320, 302, the opto-couplers 332, 318, 298 will respond to the 8–15VDC signal range that will appear on the probe status input terminals 336, 322, 306. The voltage level of the signal appearing on probe statue terminals 336, 322, 306 will depend upon the number of parallel probe electronic assemblies 206 coupled to control assembly 204. Opto-couplers 332, 318, 298 also provide complete voltage isolation between the control assembly 204 secondary circuits and probe status input terminals 336, 322, 306. Illustratively, each opto-coupler 298, 318, 332 is a TIL 116 of the type manufactured by Texas Instruments.

Zener diode 260, which is illustratively a 15 volt zener diode, clamps the control assembly 204 and relay voltages to 15 volts or less. Zener diode 340, which is illustratively a 15 volt zener diode, limits the voltage provided to the probe electronics assembly 206 to 15 volts or less so as to not exceed the 15 volt maximum operating limit for CMOS components. An additional redundant zener diode (15V) could be placed in parallel with zener diode 340 to further enhance the intrinsic safety of the system. Presently, under FM or UL double fault conditions, if zener diodes 260, 340 opened (failed) simultaneously, the open-circuit ignition voltage at the control assembly 204 power output terminal 342 would be approximately 33 volts under a worst case (high line voltage = 140 VAC) condition. With the addition of the third, redundant zener, the output (open-circuit) at power output terminal 342 would always be clamped at 15 volts regardless of which two of the three zeners failed.

Switch 230 provides the capability for disabling the audible alarm. Switch 300 provides for manual operation of relay 284. Switch 286 provides for latching of relay 284 when the input signal on terminal status input terminal 306 indicates that a hydrocarbon detection is made. IC 278 provides for up to 5 seconds of delay when a hydrocarbon is detected before energizing relay 284, LED 214, and alarm 228. This avoids false alarms caused by transients and the like. Contacts 279 of relay 284 can be utilized to provide a control signal for such purposes as controlling a sump pump as was described with respect to the embodiment shown in FIG. 1.

Although the invention has been described in detail with reference to certain preferred embodiments and specific examples, variations and modifications exist within the scope and spirit of the invention as described and as defined in the following claims.

What is claimed is:

1. An apparatus for sensing the presence of polar and non-polar fluids comprising:
a control assembly, a plurality of probe assemblies, each probe assembly located at a different location remote from said control assembly, and means for coupling each of the probe assemblies to the control assembly;
each of said probe assemblies comprising:
probe means;
polar-non-polar fluid detecting means electrically connected to said probe means for sensing the difference between a polar and non-polar fluid and for providing a fluid polar characteristic related signal;
indicating means for providing a visual or audio indication of the presence of a polar or non-polar fluid; and
manually operable test means for activating said probe indicating means to determine which probe assembly has sensed a non-polar fluid.

2. The apparatus of claim 1 and said probe assembly further comprising fluid state detecting means for detecting the state of a fluid and signal means for providing a fluid state related signal.

3. The apparatus of claim 2 and further including logic means responsive to the fluid polar characteristics related signal and the fluid state related signal for providing a plurality of probe status signals and wherein said indicating means is responsive to said probe status signals for indicating a non-liquid state of the fluid, the presence of a polar liquid, and the presence of a non-polar liquid.

4. The apparatus of claim 1 wherein said polar-nonpolar fluid detecting means comprises oscillator means for providing an oscillating electrical signal to said probe means.

* * * * *